US009605091B2

(12) United States Patent
Marissal et al.

(10) Patent No.: US 9,605,091 B2
(45) Date of Patent: Mar. 28, 2017

(54) SEPARATION OF MONOMER COMPONENTS FROM LIGHT COMPONENTS

(71) Applicant: Ineos Europe AG, Vaud (CH)

(72) Inventors: Daniel Marissal, Casteau (BE); Philip Van Breuseghem, Temse (BE); Brent R. Walworth, Belgium (BE)

(73) Assignee: INEOS EUROPE AG, Vaud (CH)

( * ) Notice: Subject to any disclaimer, the term of this patent is extended or adjusted under 35 U.S.C. 154(b) by 0 days.

(21) Appl. No.: 15/141,017

(22) Filed: Apr. 28, 2016

(65) Prior Publication Data

US 2016/0237182 A1    Aug. 18, 2016

Related U.S. Application Data

(63) Continuation of application No. 14/382,114, filed as application No. PCT/EP2013/054645 on Mar. 7, 2013, now Pat. No. 9,328,183.

(30) Foreign Application Priority Data

| Mar. 16, 2012 | (EP) | ................................. | 12159940 |
| Mar. 16, 2012 | (EP) | ................................. | 12159942 |
| Mar. 16, 2012 | (EP) | ................................. | 12159944 |

(51) Int. Cl.
| C08F 6/00 | (2006.01) |
| C08F 2/01 | (2006.01) |
| C08F 2/06 | (2006.01) |
| C07C 7/00 | (2006.01) |
| C07C 11/04 | (2006.01) |
| C07C 11/06 | (2006.01) |
| C08F 210/16 | (2006.01) |
| C08F 10/00 | (2006.01) |

(52) U.S. Cl.
CPC ................ C08F 6/005 (2013.01); C07C 7/00 (2013.01); C08F 2/01 (2013.01); C08F 2/06 (2013.01); C08F 6/001 (2013.01); C08F 10/00 (2013.01); C08F 210/16 (2013.01); Y02P 20/582 (2015.11)

(58) Field of Classification Search
CPC ......... C07C 7/005; C07C 11/04; C07C 11/06; C08F 6/001; C08F 10/02; B01D 2257/7022
See application file for complete search history.

(56) References Cited

U.S. PATENT DOCUMENTS

| 3,152,872 A | 10/1964 | Scoggin et al. |
| 3,842,060 A | 10/1974 | McDonald et al. |
| 4,087,602 A * | 5/1978 | Mietzner ................. B01J 8/005 526/352 |
| 4,182,810 A | 1/1980 | Willcox |
| 4,215,207 A | 7/1980 | Durand et al. |
| 4,424,341 A | 1/1984 | Hanson et al. |
| 4,589,957 A | 5/1986 | Sherk et al. |
| 6,042,790 A | 3/2000 | Hottovy et al. |
| 6,262,191 B1 | 7/2001 | Hottovy et al. |
| 2003/0191251 A1 | 10/2003 | McGrath |
| 2007/0142576 A1 | 6/2007 | Tait et al. |

FOREIGN PATENT DOCUMENTS

| CN | 1622854 A | 6/2005 |
| EP | 2 336 201 A1 | 6/2001 |
| EP | 2 336 200 A1 | 6/2011 |
| WO | WO 94/28032 A1 | 12/1994 |
| WO | WO/99/60028 A2 | 11/1999 |
| WO | WO 00/42077 A1 | 7/2000 |
| WO | WO 00/53306 A1 | 9/2000 |
| WO | WO 03/070365 A1 | 8/2003 |
| WO | WO 2004/039847 A1 | 5/2004 |
| WO | WO 2005/003188 A1 | 1/2005 |
| WO | WO 2006/015807 A1 | 2/2006 |
| WO | WO 2009/070261 A2 | 6/2009 |
| WO | WO 2009/070261 A3 | 6/2009 |
| WO | WO 2009/070261 A8 | 6/2009 |
| WO | WO 2011/076371 A1 | 6/2011 |

OTHER PUBLICATIONS

Specification of Co-pending National Phase U.S. Appl. No. 14/382,147, filed Aug. 29, 2014; PCT Int'l Application No. PCT/EP2013/054649, WO 2013/135564 A1, filed Mar. 7, 2013; 22 pgs.
Specification of Co-pending National Phase U.S. Appl. No. 14/382,185, filed Aug. 29, 2014; PCT Int'l Application No. PCT/EP2013/054650, WO 2013/135565 A1, filed Mar. 7, 2013; 22 pgs.

* cited by examiner

Primary Examiner — Fred M Teskin
(74) Attorney, Agent, or Firm — Nixon & Vanderhye P.C.

(57) ABSTRACT

Process for enhancing the separation of monomer components from light components other than monomer by providing a first stream containing monomer and light components other than monomer and passing the first stream to a first separator at a first pressure to separate a gaseous second stream containing at least some of the light components other than monomer and provide a liquid third stream containing monomer. A portion of the third stream and a fourth stream containing monomer and light components other than monomer is passed to a second separator at a second pressure which is lower than the first pressure to separate a gaseous fifth stream containing at least some of the light components other than monomer from the fourth stream and provide a liquid sixth stream containing monomer.

25 Claims, No Drawings

SEPARATION OF MONOMER COMPONENTS FROM LIGHT COMPONENTS

This application is a continuation of application Ser. No. 14/382,114 filed Aug. 29, 2014, U.S. Pat. No. 9,328,183, which is a 371 of PCT/EP2013/054645 filed Mar. 7, 2013, which claims priority to European Patent Application Nos. 12159940.1 filed Mar. 16, 2012, 12159942.7 filed Mar. 16, 2016 and 12159944.3 filed Mar. 16, 2013, the entire contents of each of which are hereby incorporated by reference.

The present invention relates to the treatment and recycle of effluent streams from a polymerisation process.

BACKGROUND OF THE INVENTION

The production of polymer powder by polymerisation reactions of monomers in the presence of catalysts is well-known. For example, processes are known and widely operated commercially using both fluidised bed reactors and slurry phase reactors.

In a slurry polymerisation process, for example, the polymerisation is conducted in a stirred tank or, preferably, a continuous loop reactor in which a slurry of polymer particles in a liquid medium comprising hydrocarbon diluent is circulated. During the course of polymerisation, fresh polymer is generated by the catalytic polymerisation of monomer and polymer product is removed from the reactor by removing a portion of the slurry.

The slurry withdrawn may be treated to separate the polymer particles from the hydrocarbon diluent and other components, such as unreacted monomers, which it is generally desired are recycled to the process.

A slurry polymerisation process generally includes feed systems for fresh monomer and comonomer, as well as for fresh inert liquids. Fresh feeds of monomer and co-monomer for example are fed to the polymerisation process to replace monomer and comonomer consumed in the reaction. Although inert liquids don't react they can be lost from the system in process purges or as residual amounts in the polymer passed to downstream storage and processing.

Process purges are required in the system to remove undesired inert components and poisons, which otherwise build up to detrimental levels in the process. Examples include inert hydrocarbons corresponding to the desired monomers and co-monomers. For example, where ethylene is used as a monomer ethane maybe present as an impurity in the ethylene feed and can also be produced in the reaction by hydrogenation of ethylene. Other hydrocarbons can be present even where the corresponding monomers are not used. For example methane and propane are often present in low levels in ethylene, and propane can also be present at low levels in isobutane.

It is desired to maintain low levels of such components, although in general the lower the level that is maintained the more other components are lost in the purges. Thus, purging is usually operated to try and maintain a balance in the system between levels of undesired compounds and losses of desired compounds.

The purges are usually applied during the effluent treatment steps in a polymerisation process. In particular, polymer withdrawn from a slurry polymerisation reaction is removed in slurry form in a liquid medium comprising inert diluent, quantities of unreacted monomer and comonomer, and components such as impurities and hydrogen. It is desired to recover the polymer solids essentially free of the other components, and to recycle as much as possible the useful hydrocarbons to the polymerisation reaction.

A common method to achieve this in slurry polymerisation is to heat the withdrawn slurry to vaporise the liquid medium, and to separate the vapour from the polymer solids. This is generally referred to as a "flash". The vapours can then be condensed and recycled to the reaction, whilst the polymer solids cart be recovered for further treatment.

It has become conventional that a first separation step is performed at a relatively high pressure, for example a high pressure flash step. The polymer solids are then usually let down in pressure to a lower pressure second separation step, which may be a lower pressure flash step or a flush step (in which a gas is contacted with the polymer to remove remaining hydrocarbons from the polymer) and remaining hydrocarbons are thereby removed from the polymer.

The pressure and temperature in the high pressure first separation step are generally selected such that the majority of the diluent, monomer and comonomer are recovered in the vapour, and said vapour can be condensed without compression for recycle to the reactor.

The hydrocarbons removed in the lower pressure second step are still present in sufficient quantities that it is economic to recover and recycle them to the process. However, the low pressure second separation step, in contrast to the high pressure recovery system, generally leads to recovered components, such as diluent, monomer and comonomer, which must be compressed or further cooled) in order to be able to condense them prior to recycle to the reactor.

("Compression" refers to a process of increasing the pressure "compressing") a gas or mixture of gases. This is a relatively energy intensive process. Once in the form of liquids, liquids can be pumped to increased pressure with relatively less difficulty. Avoiding "compression", for example by condensing without compression, is highly desirable.)

Examples of such systems can be found, for example, in WO 2005/003188 which discloses the use of a higher pressure flash stage followed by a lower pressure flush stage. However, processes are also known where the lower pressure stage is a flash stage rather than a flush stage, or where both flashing and flushing occur in a single stage. (It can be noted that a flush stage can also be referred to as a "purge stage". The term "flush" is used herein for such steps to avoid confusion with process purges, which are steps whereby streams are removed from a polymerisation process, for example to flare. The term "purge" as used herein therefore refers to a stream which is removed from the process rather than a flush step.)

Treatments which may be applied to one or both of the separated streams prior recycle, or at least portions thereof, include treatments to separate components such as "heavy" hydrocarbons and "light" hydrocarbons. The separated heavy and light hydrocarbons are generally purged, usually to flare.

As noted above, the use of a high pressure separation step minimises the compression required to recycle the separated vapours, and it is generally desired that as much of the liquid medium is recovered in this step as possible. Removal of significantly in excess of 90% of the liquid medium is obtainable.

SUMMARY OF THE INVENTION

We have now surprisingly found that the treatment process can be advantageously operated by deliberately letting down in pressure a portion of a recovered high pressure recycle stream, and passing this to a low pressure treatment system.

Thus, in a first aspect, there is provided a polymerisation process comprising the steps of:
1) Polymerising a monomer and a comonomer in a polymerisation reaction,
2) Withdrawing an effluent stream comprising solid polymer and a mixture comprising unreacted monomer and unreacted comonomer, and passing the effluent to a high pressure recovery system comprising
   a. a high pressure separation step for separating a vapour comprising unreacted monomer and unreacted comonomer from said solids, and
   b. a high pressure recycle system for recycling a portion of the vapour to the polymerisation reaction,
3) Passing the solids from the high pressure recovery system to a low pressure recovery system comprising
   a. a low pressure separation step for separating further unreacted monomer and unreacted comonomer from said solids, and
   b. a low pressure recycle system for recycling at least a portion of the unreacted monomer and unreacted comonomer to the polymerisation reaction,
characterised in that a portion of the vapour separated in step 2(a) is passed to the low pressure recovery system.

The polymerisation process is preferably a slurry polymerisation process, in which case the polymerisation process may comprise the steps of:
1) Polymerising a monomer and a comonomer in the presence of a diluent in a polymerisation reaction,
2) Withdrawing an effluent stream comprising solid polymer and a mixture comprising diluent, unreacted monomer and unreacted comonomer, and passing the effluent to a high pressure recovery system comprising
   a. a high pressure separation step for separating a vapour comprising diluent, unreacted monomer and unreacted comonomer from said solids, and
   b. a high pressure recycle system for recycling a portion of the vapour to the polymerisation reaction,
3) Passing the solids from the high pressure recovery system to a low pressure recovery system comprising
   a. a low pressure separation step for separating further diluent, unreacted monomer and unreacted comonomer from said solids, and
   b. a low pressure recycle system for recycling at least a portion of the further diluent, unreacted monomer and unreacted comonomer.

DETAILED DESCRIPTION OF THE INVENTION

In general, the terms "high pressure" and "low pressure" are used herein to indicate the relative pressures of two systems rather than the absolute pressures. The pressure differential between the high and low pressure recovery systems is generally at least 0.2 MPa (2 bar), preferably at least 0.4 MPa (4 bar).

As noted previously, the pressure and temperature in the high pressure separation step/high pressure recovery system are generally selected such that the majority of the diluent, monomer and comonomer are recovered in the vapour, and said vapour can be condensed without compression for recycle to the reactor.

In this context, "high pressure" generally refers to streams and stages which are at a pressure of 0.5 MPa (5 bar) and above. Usually the pressure is 0.7 MPa (7 bar) and above. There is no specific maximum pressure, but for practical purposes the term "high pressure" is usually less 2 MPa (20 bar), and usually less than 1.5 MPa (15 bar).

The low pressure recovery system, in contrast to the high pressure recovery system, leads to recovered components, such as diluent, monomer and comonomer, at significantly lower pressures.

In this context, "low pressure" generally refers to streams and stages which are at a pressure of less than 0.5 MPa (5 bar), usually less than 0.4 MPa (4 bar). Although pressures less than atmospheric pressure are possible, the "low pressure" systems are usually at a pressure of at least 0.1 MPa (1 bar).

For avoidance of any doubt, unless otherwise indicated, values of pressure as quoted herein are "absolute" values rather than "gauge" values.

The portion of the vapour separated in step 2(a) which is passed to the low pressure recovery system generally comprises at least 0.596 by weight of the vapour separated in step 2(a), such as at least 1% by weight or at least 5% by weight of the vapour separated in step 2(a).

The portion of the vapour separated in step 2(a) which is passed to the low pressure recovery system usually comprises at least 10% by weight of the vapour separated in step 2(a), preferably at least 20% by weight, such as between 20 and 40v/t% and most preferably 20 to 30wt % of the vapour separated in step 2(a).

The majority of the vapour separated in step 2(a) is recycled to the polymerisation reaction whilst maintaining pressure at or above 0.5 MPa (5 bar), preferably at or above 0.7 MPa (7 bar). The stream may thus be considered as a high pressure recycle stream.

The portion recycled to the polymerisation reaction preferably comprises the majority of the vapour from step 2(a), and most preferably at least 60%, such as at least 70% of the vapour separated in step 2(a).

Portions may however be taken from this stream to treatment steps, for example to produce an olefin-free diluent stream.

In particular, all or a portion may be cooled and taken to a (first) separator from which at least a portion of the light components other than monomer are removed to leave a condensed liquid recycle stream. All or a portion of the light components removed may be purged from the process as a purge stream, preferably to flare.

The term "separator" as used herein means a process unit in which separation of gas and liquid streams can occur. Examples of "separators" include gas/liquid separation vessels and fractionation columns.

In particular, the first separator is preferably a "high pressure separator" by which is meant a separator operated at a pressure of 0.5 MPa (5 bar) and above. Preferably, the separator is operated at a pressure of 0.7 MPa (7 bar) and above.

In general terms, the term "lights" as used herein means propane and molecules having a molecular weight less than propane. The portion of the light components other than monomer which may be removed in the separator in the present invention generally comprises light components such hydrogen, nitrogen and methane. The first separator may therefore be considered as a first "lights separator", by which as used herein is meant a separator which is operated to provide a separation of hydrogen, nitrogen and methane from monomer and heavier components present. The general concept of "lights separators" for separation of light components in polymerisation processes is well-known (along with "heavies separators" for separation of "heavy"

components). One example of such a system is taught by U.S. Pat. No. 6,292,191 although in this document the lights column is operated to remove hydrogen, oxygen, nitrogen and ethylene from diluent to give a purified, olefin-free, diluent stream, whereas in the present invention it is desired to maintain monomer in the liquid stream.

The vapour comprising light components recovered from the first separator is preferably further cooled to less than −0° C., whilst maintaining pressure at 0.5 MPa (5 bar) and above, preferably 0.7 MPa (7 bar) and above. This may then be passed to a further separator in the high pressure recovery system. Condensed liquid from the further separator is recycled to the first separator, whilst overhead vapour is passed to flare. This stream is referred to as the high pressure flare stream.

In general, light components, such as hydrogen, methane and nitrogen can be separated with very high specificity into the high pressure flare, stream, and in particular at least 75% of each of such components fed to the further separator are passed into the high pressure flare stream. As a particular example, at the temperature and pressure of the separation step the vapour stream typically comprises over 95%, of the hydrogen fed to the further separator.

Similarly, any heavy components, such as 1-hexene and hexane where present, can separate with very high specificity into the liquid stream exiting the first separator, by which is meant greater than 95% of each of such components fed to the first separator are recovered in the liquid stream.

According to the present invention a portion of the vapour separated in the high pressure recovery system is passed to the low pressure recovery system.

For avoidance of doubt, although it should be clear from the above, the reference to passing "a portion of the vapour separated in step 2(a)" to the low pressure recovery system does not mean that the separated vapour remains in the vapour state after separation in step 2(a). In particular, it is preferred that the vapour separated in the high pressure recovery system is condensed, and then a portion thereof is separated, let-down in pressure and then passed to the low pressure recovery system.

More preferably, the portion of the vapour separated in the high pressure recovery system which is passed to the low pressure recovery system is a portion separated from the liquid stream recovered from the first separator described above.

In general, letting down a portion of the recovered vapour/condensed liquid would be expected to be disadvantageous because any recovered streams let-down in pressure have to be recompressed to hero-used. To avoid the requirement for this as much as possible is exactly the reason why high pressure separation systems are used to try to maximise high pressure recovery of reaction components in the first place.

Surprisingly, however, it has been found that passing a portion of the vapour recovered at pressure to the low pressure recovery system results in improvements in the overall separations, and in particular in the ability to purge undesired components from the high pressure and low pressure recovery systems with reduced loss of useful components.

In particular, it is believed that the portion of the vapour separated in the high pressure recovery system is relatively unsaturated in monomer. When let down to the lower pressure and passed to the low pressure recovery system there is an increase in the overall recovery of monomer for recycle.

The additional recovery of monomer leads to a reduction in monomer losses in the process purges. Whilst monomer efficiencies of polymerisation processes, which is calculated herein as the amount of monomer fed which is not purged, are generally very high (above 98.5%), at the scale of commercial polymerisation processes even what appears as relatively minor increases in efficiency can result in significant cost savings, as well as significant reductions in hydrocarbon emissions or combustion products from hydrocarbon emissions (when flared). For example, in a process producing 50 tonnes/hour of polymer, an increase in monomer efficiency by only 0.1% is still a reduction in monomer losses of 50 kg/hour.

More particularly, the process of the present invention is able to provide a monomer efficiency in excess of 99.5%, for example of 99.6% and above, and most preferably of 99.7% and above.

The monomer efficiency is a measure of the amount of the monomer which ends up in the polymer product, and is determined from the amount of fresh monomer fed to a process and the amount of monomer which is purged. The monomer purge rate may be determined from the purge flow and the concentration of monomer in the purge stream, which can be measured by GC, for each purge stream present. The efficiency may be determined instantaneously, based on flow rate measurements at a particular time, but preferably is determined over a period of time, for example based on averaged instantaneous measurements or on total amounts fed and purged determined over a period of at least several hours, as this generally gives a more accurate measurement. The monomer efficiency is determined by subtracting the amount purged from the amount fed, and then dividing the result by the amount fed. This answer is multiplied by 100 to give the efficiency as a percentage.

Similarly, the process of the present invention can provide an increase in comonomer efficiency, which as used herein as the amount of comonomer fed which is not purged. More particularly the process of the present invention is able to provide a comonomer efficiency in excess of 95%, for example of 97% and above, and most preferably of 98% and above.

The portion of the vapour separated in step 2(a) which is passed to the low pressure recovery system is preferably passed to the low pressure recycle system part of the pressure recovery system. Put another way, the portion of the vapour separated in step 2(a) is preferably not passed to the low pressure separation step (step 3(a)) for separating further unreacted monomer and unreacted comonomer from the solids.

The portion of the vapour separated in step 2(a) which is passed to the low pressure recovery system is preferably passed to a low pressure and low temperature separator in the low pressure recovery system (also referred to herein as a "second separator"). In particular, the present invention preferably comprises a low pressure recovery system which comprises a second separator which is at a pressure of less than 0.4 MPa (4 bar) and at a temperature of less than −10° C. (The second separator is a part of the low pressure recovery system.)

The second separator may also be considered as a second "lights separator", which is operated to provide a separation of light compounds such as hydrogen, nitrogen and methane as already defined.

The majority of light components other than monomer, such as nitrogen, hydrogen and methane are again recovered as an overhead vapour stream. A portion of this stream is purged from the system, preferably to a flare.

Although the first and second separator generally result in hydrogen passing the overhead streams, and hence to any purge streams, the quantities of hydrogen in the process is generally small, and the hydrogen is more cost effectively flared than recycled and recovered to the overall polymerisation process. In fact, a further advantage of the present invention is that the purging of hydrogen is efficient enough that other impurities which can be present in fresh hydrogen feeds, such as methane and CO, can also be efficiently purged from the system via the purge streams, and the separate purification of fresh hydrogen feed to remove such components can be reduced or avoided.

Thus, a low hydrogen efficiency of a polymerisation process has also been found to be advantageous.

The process of the present invention preferably has a hydrogen efficiency, measured as the amount of the fed hydrogen which is not purged of 80% or less, preferably of 70% or less, and most preferably of 60% or less.

The hydrogen efficiency may be determined in a similar manner to the monomer efficiency, and in particular by determining the amount of hydrogen purged from the purge flow and the hydrogen concentration in the purge stream, which can be measured by GC, for each purge stream present and comparing this to the amount of hydrogen fed to the process.

The combination of the first and second separators described above is particularly preferred. Thus, in a preferred embodiment the present invention provides a polymerisation process comprising the steps of:

1) Polymerising a monomer and a comonomer in a polymerisation reaction,
2) Withdrawing an effluent stream comprising solid polymer and a mixture comprising unreacted monomer and unreacted comonomer, and passing the effluent to a high pressure recovery system comprising
   a. a high pressure separation step for separating a first vapour stream comprising unreacted monomer and unreacted comonomer from said solids, and
   b. a high pressure recycle system for recycling a portion of the first vapour stream to the polymerisation reaction, said high pressure recycle system comprising
      i. a first separator at a pressure greater than 0.5 MPa (5 bay) for separating a second vapour stream comprising at least a portion of light components other than monomer in the first vapour stream and a liquid stream comprising condensed portions of the first vapour stream,
3) Passing the solids from the high pressure recovery system to a low pressure recovery system comprising
   a. a low pressure separation step for separating further unreacted monomer and unreacted comonomer from said solids, and
   b. a low pressure recycle system for recycling at least a portion of the further unreacted monomer and unreacted comonomer to the polymerisation reaction, said low pressure recycle system comprising
      i. a second separator which operates at a pressure of less than 0.5 MPa (5 bar), preferably less than 0.4 MPa (4 bar), and at a temperature of less than −10° C.

characterised in that a portion of the liquid stream from step 2(b)(i) is passed to the second separator.

Further, the present invention provides a process for enhancing the separation of monomer components from light components other than monomer, which process comprises:

A) Providing a first stream comprising monomer and light components other than monomer B) Passing the first stream to a first separator at a first pressure to separate a second stream comprising at least some of the light components other than monomer and provide a third stream comprising monomer,
C) Passing a portion of the third stream and a fourth stream comprising monomer and light components other than monomer to a second separator at a second pressure which is Lower than the first pressure to separate a fifth stream comprising at least some of the light components other than monomer from the fourth stream and provide a sixth stream comprising monomer.

In this aspect of the present invention the first stream comprising monomer and light components other than monomer is passed to a first separator to separate at least some of the Light components other than monomer therein, and then a portion of the recovered third stream is reduced in pressure and passed with a fourth stream also comprising monomer and light components other than monomer to a second separator.

The process of this aspect of the invention results in a reduction in the concentration of monomer in the combined second and fifth streams compared to a process where the first and fourth streams are passed separately to the first and second separators without passing a portion of the third stream to the second separator.

The first pressure is higher than the second pressure, Preferably the first pressure is at least 0.5 MPa (5 bar). Preferably the second pressure is less than 0.5 MPa (5 bar), and more preferably is less than 0.4 MPa (4 bar). Preferably the pressure difference between the first and second pressures is at least 0.2 MPa (2 bar), more preferably at least 0.3 MPa (3 bar).

The second separator is preferably at a pressure of less than 0.4 MPa (4 bar) and a temperature of less than 10° C.

The monomer in the process of the present invention is preferably an olefin monomer. For avoidance of any doubt, the term "monomer" as used herein refers to the olefin which is present in the largest amount in the formed polymer, and may also be referred to as the "principal monomer", whilst the term "comonomer" as used herein refers to olefins other than the monomer which may be present. More than one comonomer may be present.

The monomer is preferably ethylene or propylene, most preferably ethylene.

Where ethylene is the monomer, propylene maybe the comonomer, but the comonomer is preferably selected from 1-butene, 1-hexene and 1-octene, with 1-hexene being most preferred.

Where propylene is the monomer, the comonomer is preferably selected from ethylene, 1-butene, 1-hexene and 1-octene.

The comonomer is preferably 1-hexene.

Preferred diluents which may be used are inert hydrocarbons, more preferably butanes, especially iso-butane, pentanes and mixtures thereof. Iso-butane is most preferred.

In a preferred embodiment of the present invention there are also passed to the "low pressure and low temperature separator" in the tow pressure recovery system one or more fresh liquid feeds for the polymerisation reaction.

"Fresh" as used herein means a component which is being passed to the reaction for the first time and can be contrasted with "recycle" streams which contain components recovered from the reaction effluent for recycle. However, for avoidance of doubt such streams may have been subjected to pre-treatments to reduce impurities.

The fresh liquids which are passed to a slurry polymerisation reaction include the diluent in the process. Such components are added to the reaction and form part of the liquid medium of the slurry in the reaction. As noted above, examples of such liquids are inert hydrocarbons, most preferred diluents including butanes, especially iso-butane, pentanes and mixtures thereof. Iso-butane is most preferred.

The fresh liquids to a slurry polymerisation reaction can also include comonomers. As noted above, commonly used comonomers include 1-butene, 1-hexene and 1-octene, although other comonomers can be used.

It is preferred that both fresh comonomer and fresh diluent are passed to the second separator.

It has been surprisingly found that passing fresh diluent and/or fresh comonomer to the second separator also improves the efficiency of the overall process in removing impurities whilst minimising losses of monomer and diluent.

Although it is possible to also feed fresh comonomer and/or fresh monomer directly to the polymerisation reaction, it is preferred in this embodiment that the majority of fresh comonomer passed to the reaction is passed via the claimed process and that the majority of fresh diluent passed to the reaction is passed via the claimed process i.e. via the second separator and most preferably via the second separator at a pressure of less than 0.4 MPa (4 bar) and at a temperature of less than −10° C.

Most preferably, it is preferred that all of the fresh comonomer passed to the reaction is passed via the claimed process and all of the fresh diluent passed to the reaction is passed via the claimed process The process of the present invention may be applied to a polymerisation process operating in one or more reactors. The operation of two loop reactors in series, for example, is well-known. The term "polymerisation reaction" as used herein is intended generically to refer to polymerisation occurring in a single reactor or polymerisation occurring in two or more reactors.

Thus, in a system comprising two or more reactors, a recycle system for recycling to "the polymerisation reaction" may recycle components to a single reactor or to both reactors in the system.

Where at least two reactors are operated in parallel then effluent stream from each may be withdrawn, combined and passed to a common recovery system (e.g. to a single high pressure recovery system and a subsequent single low pressure recovery system).

Where at least two reactors are operated in series, then an effluent stream is usually withdrawn from the last reactor in series for passage to the high pressure recovery system (and then to the low pressure recovery system. Effluent withdrawn from an earlier reactor in series is generally passed to a subsequent reactor in the series, although intermediate treatments are possible, for example to remove hydrogen or comonomer. (Such treatments may, in fact, be required depending on the particular process being operated.)

EXAMPLES

General Process

Ethylene is polymerised in two slurry loop reactors in series to produce a bimodal polyethylene with a density of 948 kg/m$^3$ and a Melt Index (MI$_5$) of 0.31.

In the first reactor ethylene is polymerised in the substantial absence of comonomer, but in the presence of hydrogen and with isobutane as diluent. Polymer from the first reactor is passed to a second reactor wherein further ethylene is polymerised in the presence of 1-hexene as comonomer and the substantial absence of hydrogen, again in the presence of isobutane.

Polymer slurry is withdrawn from the first reactor and passed to a contacting vessel in the form of a stirred tank.

Polymer slurry is recovered from the base of the contacting vessel and passed to the second reactor.

Polymer slurry is withdrawn from the second reactor and passed via a slurry heater, in which the liquid components of the slurry are vaporised, to a flash tank at a pressure of 0.95 MPa.

Polymer solids are withdrawn from the flash tank for further processing.

The vapour recovered from the flash tank is passed as the first vapour to the contacting vessel where it is contacted with the slurry withdrawn from the first reactor.

Vapour is withdrawn from the top of the contacting tank and passed to a fractionator in which it is contacted with a reflux stream. Liquids recovered from the base of the fractionator are returned to the contacting tank.

The combined "contacting tank/fractionator" is herein referred to as a "fractionation system".

Vapour recovered overhead from the fractionator is cooled and partially condensed, then passed to a liquid/vapour (first) separator operating at a temperature of 35° C. and a pressure of 0.91 MPa.

A portion of the liquid recovered therefrom is utilised as the reflux stream to the fractionator.

The vapour recovered from the liquid/vapour separator is further cooled and separated at −35° C. and 0.91 MPa in a further separator in the high pressure recovery system. Condensed liquid is recycled to the liquid/vapour first separator, whilst overhead vapour is passed to flare. This stream is referred to as the high pressure flare stream.

Polymer solids withdrawn from the flash tank are passed for further processing in a flush vessel at a pressure of 0.135 MPa. The flushing takes place by contact in two vertically orientated stages with polymer being introduced at the top and withdrawn from the base of the vessel, and with a recycled flush gas being introduced into the upper stage and nitrogen being introduced into the lower stage.

A mixture of the flush gases and recovered diluent/monomer is recovered from the top of the flush vessel, cooled and passed to low pressure treatment steps. A portion is passed to a heavies separation unit to remove heavy components, but the majority (including a recycle stream from the heavies separation unit) is passed to a (second) separator at a pressure of 0.40 MPa and at a temperature of −30° C.

From the base of the second separator is recovered a liquid stream which can be recompressed and recycled to the second reactor.

Overhead from the second separator is recovered a vapour stream. The majority of this stream is recycled to the flush vessel, but a portion is passed to a flare. This stream is referred to as the low pressure flare stream.

Comparative Example

In a Comparative Example a portion of the condensed liquid recovered in the high pressure recovery system from the liquid/vapour separator (at a temperature of 35° C. and a pressure of 0.91 MPa) is taken and treated, but the remainder is pumped back to a higher pressure and recycled to the first reactor.

The composition of the high pressure and low pressure flare streams are shown in Table 1

Example According to the Invention

In this Example a portion of the condensed liquid recovered in the high pressure recovery system from the liquid/vapour first separator (at a temperature of 35° C. and a pressure of 0.91 MPa) is taken and treated as in the Comparative Example. A further portion is let-down in pressure and fed to the low pressure recovery system, and in particular is combined with the majority of the stream recovered from the flush vessel which is passed to the second separator (at a pressure of 0.40 MPa and at a temperature of −30° C.). The reminder of the condensed liquid recovered in the high pressure recovery system from the liquid/vapour separator is pumped back to a higher pressure and recycled to the first reactor as in the Comparative Example. In order to balance the overall process the amount taken and utilised as the reflux stream to the fractionator is reduced.

The further portion passed to the low pressure recovery system comprises about 27% of the condensed liquid recovered from the liquid/vapour first separator.

The composition of the high pressure and low pressure flare streams are shown in Table 2.

TABLE 1

| Component | High pressure flare stream (kg/h) | Low pressure flare stream (kg/h) | Total |
|---|---|---|---|
| Nitrogen | 21.40 | 268.09 | 289.52 |
| Ethylene | 293.03 | 16.90 | 309.93 |
| Ethane | 94.46 | 2.62 | 97.08 |
| Propane | 1.96 | 0.66 | 2.63 |
| Iso-butane | 39.92 | 63.43 | 103.35 |
| 1-hexene |  | 0.84 | 0.84 |
| Hexane |  | 0.03 | 0.03 |
| Methane | 15.87 | 0.33 | 16.2 |
| Hydrogen | 12.89 | 0.02 | 12.91 |

TABLE 2

| Component | High pressure flare stream (kg/h) | Low pressure flare stream (kg/h) | Total |
|---|---|---|---|
| Nitrogen | 61.55 | 227.96 | 289.51 |
| Ethylene | 162.67 | 50.57 | 213.24 |
| Ethane | 69.58 | 27.42 | 97.00 |
| Propane | 1.40 | 1.55 | 2.94 |
| Iso-butane | 35.37 | 84.84 | 120.22 |
| 1-hexene |  | 0.16 | 0.16 |
| Hexane |  | 0.01 | 0.01 |
| Methane | 13.86 | 2.30 | 16.16 |
| Hydrogen | 12.12 | 0.52 | 12.64 |

Comparing the results in Tables 1 and 2, similar amounts of nitrogen, ethane and hydrogen are purged overall, but the total ethylene losses in the purges are reduced by 31% (from 310 kg/h to 213 kg/hr).

The reduction in the total ethylene losses in the Example compared to the Comparative Example corresponds to a monomer efficiency increase from 99.3 to 99.6%.

The losses of 1-hexene are also reduced, in particular from 0.84 to 0.16 kg/hr. The reduction in the total 1-hexene losses Example compared to the Comparative Example corresponds to a comonomer efficiency increase from about 95 to about 99%.

The invention claimed is:

1. A process for enhancing the separation of monomer components from light components other than monomer, which process comprises:
    A) Providing a first stream comprising monomer and light components other than monomer,
    B) Passing the first stream to a first separator at a first pressure to separate a gaseous second stream comprising at least some of the light components other than monomer and provide a liquid third stream comprising monomer,
    C) Passing a portion of the third stream and a fourth stream comprising monomer and light components other than monomer to a second separator at a second pressure which is lower than the first pressure to separate a gaseous fifth stream comprising at least some of the light components other than monomer from the fourth stream and provide a liquid sixth stream comprising monomer.

2. A process according to claim 1 wherein the first pressure is at least 0.5 MPa (5 bar).

3. A process according to claim 1 wherein the second pressure is less than 0.5 MPa (5 bar).

4. A process according to claim 1 wherein the pressure difference between the first and second pressures is at least 0.2 MPa (2 bar).

5. A process according to claim 1 wherein the second separator is at a pressure of less than 0.4 MPa (4 bar) and a temperature of less than 10° C.

6. A process according to claim 1 wherein the monomer is ethylene or propylene.

7. A process according to claim 1 wherein fresh diluent and/or fresh comonomer is passed to the second separator.

8. A process according to claim 1 which is applied to a polymerisation process operating in one or more reactors.

9. A process according to claim 8 wherein there are at least two reactors operating in series.

10. A process according to claim 8 which has a monomer efficiency in excess of 99.5%.

11. A process according to claim 8 wherein comonomer is fed to the polymerisation process and the process has a comonomer efficiency in excess of 95%.

12. A process according to claim 8 wherein the first separator is operated to provide a separation of hydrogen, nitrogen and methane from monomer and heavier components.

13. A process according to claim 8 wherein the second stream is cooled to less than −10° C. whilst maintaining pressure at 0.5 MPa (5 bar) and above.

14. A process according to claim 8 wherein the second separator is at a pressure of less than 0.4 MPa (4 bar) and at a temperature of less than −10° C.

15. A process according to claim 8 comprising:
    1) Polymerising a monomer and a comonomer in a polymerisation reaction,
    2) Withdrawing an effluent stream comprising solid polymer and a mixture comprising unreacted monomer and unreacted comonomer, and passing the effluent to a high pressure recovery system comprising
        a. a high pressure separation step for separating a first vapour stream comprising unreacted monomer and unreacted comonomer from said solids, and
        b. a high pressure recycle system for recycling a portion of the first vapour stream to the polymerisation reaction, said high pressure recycle system comprising
            i. the first separator at a pressure greater than 0.5 MPa (5 bar) for separating the second stream comprising at least a portion of light components other than monomer in the first vapour stream and the third stream which is a liquid stream comprising condensed portions of the first vapour stream,
3) Passing the solids from the high pressure recovery system to a low pressure recovery system comprising
   a. a low pressure separation step for separating further unreacted monomer and unreacted comonomer from said solids, and
   b. a low pressure recycle system for recycling at least a portion of the further unreacted monomer and unreacted comonomer to the polymerisation reaction, said low pressure recycle system comprising
      i. the second separator which operates at a pressure of less than 0.5 MPa (5 bar) and at a temperature of less than −10° C.

16. A process according to claim 15 wherein at least two reactors are operated in parallel and effluent stream from each is withdrawn, combined and passed to a common recovery system.

17. A process according to claim 15 wherein at least two reactors are operated in series, and an effluent stream is withdrawn from the last reactor in series for passage to the high pressure recovery system and then to the low pressure recovery system.

18. A process according to claim 15 wherein the portion of the third stream which is passed to the second separator comprises at least 1% by weight of the vapour separated in step 2(*a*).

19. A process according to claim 15 wherein the portion of the third stream which is passed to the second separator comprises between 20 and 40 wt % of the vapour separated in step 2(*a*).

20. A process according to claim 15 wherein a portion of the overhead stream from the separator in the low pressure recovery system is purged from the system.

21. A process according to claim 3 wherein the second pressure is less than 0.4 MPa (4 bar).

22. A process according to claim 4 wherein the pressure difference between the first and second pressures is at least 0.3 MPa (3 bar).

23. A process according to claim 6 wherein the monomer is ethylene.

24. A process according to claim 14 wherein the second separator is part of a low pressure recovery system.

25. A process according to claim 15 wherein the second separator operates at a pressure of less than 0.4 MPa (4 bar).

* * * * *